United States Patent
Lee et al.

(10) Patent No.: US 8,932,434 B2
(45) Date of Patent: *Jan. 13, 2015

(54) DIVIDING WALL DISTILLATION COLUMN FOR PRODUCING HIGH PURITY ACRYLIC ACID AND FRACTIONAL DISTILLATION METHOD USING THE SAME

(75) Inventors: Sung Kyu Lee, Daegu (KR); Jong Ku Lee, Daejeon (KR); Joon Ho Shin, Daejeon (KR)

(73) Assignee: LG Chem, Ltd., Seoul (KR)

( * ) Notice: Subject to any disclaimer, the term of this patent is extended or adjusted under 35 U.S.C. 154(b) by 502 days.

This patent is subject to a terminal disclaimer.

(21) Appl. No.: 13/256,431

(22) PCT Filed: Mar. 19, 2010

(86) PCT No.: PCT/KR2010/001727
§ 371 (c)(1),
(2), (4) Date: Sep. 13, 2011

(87) PCT Pub. No.: WO2010/107284
PCT Pub. Date: Sep. 23, 2010

(65) Prior Publication Data
US 2012/0006673 A1    Jan. 12, 2012

(30) Foreign Application Priority Data

Mar. 19, 2009 (KR) .................. 10-2009-0023457
Mar. 19, 2010 (KR) .................. 10-2010-0024596

(51) Int. Cl.
*B01D 3/14* (2006.01)
*C07C 57/04* (2006.01)
*C07C 51/44* (2006.01)

(52) U.S. Cl.
CPC . *B01D 3/14* (2013.01); *C07C 57/04* (2013.01); *B01D 3/141* (2013.01); *C07C 51/44* (2013.01)
USPC ............... 203/87; 203/99; 202/158; 202/161; 202/262; 562/600

(58) Field of Classification Search
CPC ......... B01D 3/141; C07C 51/44; C07C 57/04
USPC ...................... 203/87, 99; 202/158, 161, 262; 562/598–600
See application file for complete search history.

(56) References Cited

U.S. PATENT DOCUMENTS 4,554,054 A    11/1985  Coyle
6,254,735 B1 *  7/2001  Watzenberger ................. 203/26
(Continued)

FOREIGN PATENT DOCUMENTS

CN    101367720 A    2/2009
JP    09-299702 A    11/1997
(Continued)

OTHER PUBLICATIONS

Lestak et al: "Advanced Distillation Saves Energy and capital", Chemical Engineering, Access Intelligence Association, Rockville, MA, US, vol. 7, Jul. 1, 1997, pp. 72-76, XP001156299.
(Continued)

*Primary Examiner* — Prem C Singh
*Assistant Examiner* — Jonathan Miller
(74) *Attorney, Agent, or Firm* — McKenna Long & Aldridge, LLP

(57) ABSTRACT

There are provided a dividing wall distillation column for producing high-purity acrylic acid, and a fractional distillation method using the same. The dividing wall distillation column includes a condenser, a reboiler and a main column having a dividing wall. Here, the main column is divided into a column-top zone, an upper feed zone, an upper outflow zone, a lower feed zone, a lower outflow zone and a column-bottom zone. Accordingly, since one distillation column can be used to realize the same effect as that obtained from the use of two distillation columns, the dividing wall distillation column can have an effect of reducing the costs of equipment to produce high-purity acrylic acid, as well as an energy-reducing effect, compared to a conventional process system.

2 Claims, 7 Drawing Sheets

(56) References Cited

U.S. PATENT DOCUMENTS

| | | | |
|---|---|---|---|
| 7,550,064 B2 * | 6/2009 | Bassler et al. | 203/29 |
| 8,242,308 B2 * | 8/2012 | Ho et al. | 562/600 |
| 8,282,793 B2 * | 10/2012 | Heydrich et al. | 203/71 |
| 8,426,637 B2 * | 4/2013 | Koestner et al. | 562/545 |
| 8,461,356 B2 | 6/2013 | Windecker et al. | |
| 8,530,700 B2 * | 9/2013 | Ho et al. | 562/600 |
| 2004/0225152 A1 | 11/2004 | Yada et al. | |
| 2013/0118892 A1 * | 5/2013 | Meier et al. | 203/53 |

FOREIGN PATENT DOCUMENTS

| | | |
|---|---|---|
| JP | 11-315051 A | 11/1999 |
| JP | 2004517136 A | 6/2004 |
| JP | 2004529129 A | 9/2004 |
| JP | 2004358387 A | 12/2004 |
| KR | 10-2003-0057363 | 7/2003 |
| KR | 10-0464841 | 4/2005 |
| TW | 200902509 A | 1/2009 |
| WO | 2008033687 A2 | 3/2008 |
| WO | WO 2008/116810 A1 | 10/2008 |
| WO | WO 200900634 A1 * | 12/2008 ............ C07C 45/82 |

OTHER PUBLICATIONS

Kaibel G: "Distillation Columns With Vertical Partitions", Chemical Engineering and Technology, Weinheim, DE, vol. 10, Jan. 1, 1987, pp. 92-98, XP002939161.

* cited by examiner

DIVIDING WALL DISTILLATION COLUMN FOR PRODUCING HIGH PURITY ACRYLIC ACID AND FRACTIONAL DISTILLATION METHOD USING THE SAME

This application is a National Stage Entry of International Application No. PCT/KR2010/001727, filed Mar. 19, 2010, and claims priority to and the benefit of Korean Patent Application Nos. 10-2009-0023457, filed on Mar. 19, 2009 and 10-2010-0024596, filed on Mar. 19, 2010, which are hereby incorporated by reference in their entirety for all purposes as if fully set forth herein.

TECHNICAL FIELD

The present invention relates to a dividing wall distillation column for producing high-purity acrylic acid and a fractional distillation method using the same.

BACKGROUND ART

In general, various source materials such as crude oil are often present as a mixture of numerous chemicals. Therefore, the source materials themselves are hardly used in industries, but are generally separated into respective compounds that are used in industries. A distillation process is representative of chemical processes for separating a mixture.

In general, the distillation process serves to separate the mixture into two components: a high boiling point component and a low boiling point component. Therefore, the distillation columns whose number (n−1) is smaller than the number (n) of components in the mixture to be separated by 1 are used. That is to say, a process for separating a three-component mixture has mainly used a structure in which two distillation columns are continuously operated on site in conventional distillation industries.

A conventional distillation process for separating a three-component mixture is shown in FIG. 1.

The conventional distillation process uses a two-column system in which a lowermost boiling point component (D) is separated in a first column 11, and a middle boiling point component (S) and a high boiling point component (B) are separated in a second column 21.

In a conventional two-column distillation system, a compositional profile of acrylic acid in a first column is shown in FIG. 2. As shown in FIG. 2, the middle boiling point component (S) may be generally remixed in a lower section of the first column.

The above-described conventional distillation process can easily control a composition of a product, but the middle boiling point component is remixed in the first distillation column. Therefore, a thermodynamic efficiency in the distillation column is degraded, resulting in unnecessary consumption of energy.

In order to solve these problems, much research on a new distillation structure has been conducted. A representative example of improving a separation efficiency using a thermally coupled structure may be a structure of a Petlyuk distillation column as shown in FIG. 3. The Petlyuk distillation column is arranged in a structure in which a preliminary separator 12 and a main separator 22 are thermally coupled. Therefore, a low boiling point component and a high boiling point component are primarily separated in the preliminary separator, and then flow to a feed plate of the main separator through a column-top portion and a column-bottom portion of the preliminary separator. Thereafter, the low boiling point, middle boiling point, and high boiling point components are separated in the main separator. This structure has high energy efficiency since a distillation curve in the Petlyuk distillation column is similar to an equilibrium distillation curve. However, the design and operation of a process are not easy, and the balance of pressure in the distillation column is particularly difficult to adjust.

In order to solve the problems regarding the Petlyuk distillation column, a dividing wall distillation column (DWC) has been proposed. A thermodynamic aspect of the DWC is similar to that of the Petlyuk distillation column, but a structural aspect is different from that of the Petlyuk distillation column in that a dividing wall is installed in a distillation column to integrate the preliminary separator of the Petlyuk distillation column in the main separator. Such a structure is highly advantageous in that operations are easily performed since the problems regarding the balance between the preliminary separator of the Petlyuk distillation column and the main separator are naturally solved and thus operations are simple, and the investment costs may also be significantly reduced since two types of distillation columns are integrated into one.

The following Documents 1 and 2 disclose a conventional technique associated with the distillation of acrylic acid.

Document 1 discloses a method of distilling and separating pure (meth)acrylic acid from a mixture. That is to say, a distillation device, which includes a thin film evaporator, a condenser, a baffle unit, and a connection unit for connecting the thin film evaporator to the condenser, is used to distill and separate pure (meth)acrylic acid from a mixture that includes (meth)acrylic acid and a dimer and oligomer of the (meth)acrylic acid and does not substantially include an aldehyde or a component having a lower boiling point than the (meth)acrylic acid.

Document 2 discloses a method of purifying a (meth)acryl monomer through distillation. The method known in the prior art includes purifying a (meth)acryl monomer, selected from (meth)acrylic acid and esters thereof, from a liquid containing a (meth)acrylic acid monomer by distilling the liquid in the presence of at least one polymerization inhibitor requiring the introduction of oxygen and/or an inhibitor showing a higher effect in the presence of oxygen so as to stabilize the liquid, wherein the distillation is performed in the presence of $NO_2$ gas at an oxygen/organic vapor ratio (W/W) of 0.02 to 3% and an $NO_2$/organic vapor ratio (W/W) of $1\times10^{-6}$ to $5\times10^{-3}$% (i.e., 0.01 to 50 PPM).
[Document 1] KR 10-1996-0047606 (filed on Oct. 23, 1996)
[Document 2] KR 10-2002-7006584 (filed on May 23, 2002)

Documents 1 and 2 are quite different from the present invention in that the methods proposed in Documents 1 and 2 are directed to a distillation column including a dividing wall.

DISCLOSURE

Technical Problem

In spite of the advantages of the above-mentioned dividing wall distillation column, the dividing wall distillation column is hardly installed on site in the distillation industry. One important reason for this is that the dividing wall distillation column is inflexible in a variation in operating conditions due to the structural characteristics in which a flow rate of an internally circulating material cannot be controlled once the dividing wall distillation column is designed, unlike the Petlyuk distillation column. That is to say, an exact simulation and a structural determination are required at the beginning of the design of the distillation column.

In recent years, much research on the structure and control of the dividing wall distillation column has been conducted, but the details of the design structures and operating conditions of the dividing wall distillation column such as a position of a feed plate, setting of a dividing wall section, a position of a plate for producing a middle boiling point component, a total number of plates, a distillation temperature and a distillation pressure are very restrictive in the distillation column.

Particularly, since the design structures such as a plate number of the distillation column and a position of a feed plate, and the operating conditions such as distillation temperature and pressure should be changed according to the natures of a compound to be fractionally distilled, it is difficult to use the dividing wall distillation column.

Therefore, in order to solve the above-mentioned problems, reduce energy consumption and the costs of equipment, the present invention is directed to providing a dividing wall distillation column having a suitable design to purify acrylic acid and a method for operating the same.

Technical Solution

Therefore, the present invention is designed to solve the above problems, and an object of the present invention is to provide a dividing wall distillation column including a condenser, a reboiler, and a main column having a dividing wall formed therein. Here, the main column is divided into a column-top zone, an upper feed zone, an upper outflow zone, a lower feed zone, a lower outflow zone and a column-bottom zone. Also, a crude acrylic acid raw material (F) flows in a middle inflow plate NR1 in which the upper feed zone and the lower feed zone come in contact with each other, a low boiling point component (D) flows out from the column-top zone, a high boiling point component (B) flows out from the column-bottom zone, and a middle boiling point component (S) flows out through a middle outflow plate NR2 in which the upper outflow zone and the lower outflow zone come in contact with each other. In this case, the middle boiling point component is acrylic acid.

Also, the raw material (F) may have an acrylic acid content of 90% by weight or more.

In addition, the number of plates provided respectively in the column-top zone, the upper feed zone, the upper outflow zone, the lower feed zone, the lower outflow zone and the column-bottom zone may be in a range of 80 to 150% of a theoretical plate number, as calculated from a distillation curve.

Additionally, a length of the dividing wall may be determined according to the total theoretical plate number in the upper feed zone and the lower feed zone.

Also, a length of the dividing wall may be in a range of 30 to 85% of the total theoretical plate number in the column-top zone, the upper feed zone, the lower outflow zone and the column-bottom zone, as calculated from the distillation curve.

In addition, a temperature of the column-top zone may be in a range of 55 to 65° C. at a pressure of 4.666 kPa.

Additionally, a temperature of the column-bottom zone may be in a range of 90 to 100° C. at a pressure of 4.666 kPa.

Moreover, a temperature of the middle outflow plate NR2, which is provided in a position where the upper outflow zone and the lower outflow zone come in contact with each other, and from which the middle boiling point component (S) flows out, may be in a range of 73 to 83° C. at a pressure of 4.666 kPa.

Also, the temperature of the column-top zone may be in a range of a lower temperature limit ($T_{1\alpha}$) to an upper temperature limit ($T_{2\alpha}$), which follows the following Equation 1, when the pressure is out of a pressure of 4.666 kPa:

Lower limit: $T_{1\alpha}=21.5052*P^{0.2628}$

Upper limit: $T_{2\alpha}=29.3928*P^{0.2222}$  Equation 1

(wherein $T_{1\alpha}$ and $T_{2\alpha}$ represent temperatures (° C.); P represents a pressure (kPa), provided that $1.333 \leq P \leq 13.332$ and $P \neq 4.666$).

In addition, the temperature of the column-bottom zone may be in a range of a lower temperature limit ($T_{1\beta}$) to an upper temperature limit ($T_{2\beta}$), which follows the following Equation 2, when the pressure is out of a pressure of 4.666 kPa:

Lower limit: $T_{1\beta}=56.3053*P^{0.1293}$

Upper limit: $T_{2\beta}=65.6035*P^{0.1163}$  Equation 2

(wherein $T_{1\beta}$ and $T_{2\beta}$ represent temperatures (° C.); P represents a pressure (kPa), provided that $1.333 \leq P \leq 13.332$ and $P \neq 4.666$).

Additionally, the temperature of the middle outflow plate NR2, which is provided in a position where the upper outflow zone and the lower outflow zone come in contact with each other, and from which the middle boiling point component (S) flows out, is in a range of a lower temperature limit ($T_{1\chi}$) to an upper temperature limit ($T_{2\chi}$), which follows the following Equation 3, when the pressure is out of a pressure of 4.666 kPa:

Lower limit: $T_{1\chi}=44.8814*P^{0.1376}$

Upper limit: $T_{2\chi}=55.0983*P^{0.1211}$  Equation 3

(wherein $T_{1\chi}$ and $T_{2\chi}$ represent temperatures (° C.); P represents a pressure (kPa), provided that $1.333 \leq P \leq 13.332$ and $P \neq 4.666$).

Another aspect of the present invention provides a method of fractionally distilling acrylic acid. Here, the method includes producing acrylic acid using the above-described dividing wall distillation column.

Advantageous Effects

According to the present invention, since one distillation column can be used to realize the same effect as that obtained from the use of two distillation columns, the dividing wall distillation column can have an effect of reducing the cost of equipment to produce high-purity acrylic acid, as well as an energy-reducing effect, compared to a conventional process system.

DESCRIPTION OF DRAWINGS

These and other features, aspects, and advantages of preferred embodiments of the present invention will be more fully described in the following detailed description, with reference to the accompanying drawings. In the drawings.

BEST MODE

Hereinafter, preferred embodiments of the present invention will be described in detail referring to the accompanying drawings.

The present invention provides a dividing wall distillation column including a condenser, a reboiler, and a main column having a dividing wall. Here, the main column is divided into a column-top zone, an upper feed zone, an upper outflow zone, a lower feed zone, a lower outflow zone and a column-bottom zone. Also, a crude acrylic acid raw material (F) flows in a middle inflow plate NR1 in which the upper feed zone and the lower feed zone come in contact with each other, a low boiling point component (D) flows out from the column-top zone, a high boiling point component (B) flows out from the column-bottom zone, and a middle boiling point component (S) flows out through a middle outflow plate NR2 in which the upper outflow zone and the lower outflow zone come in contact with each other. In this case, the middle boiling point component is acrylic acid.

Figure 1:
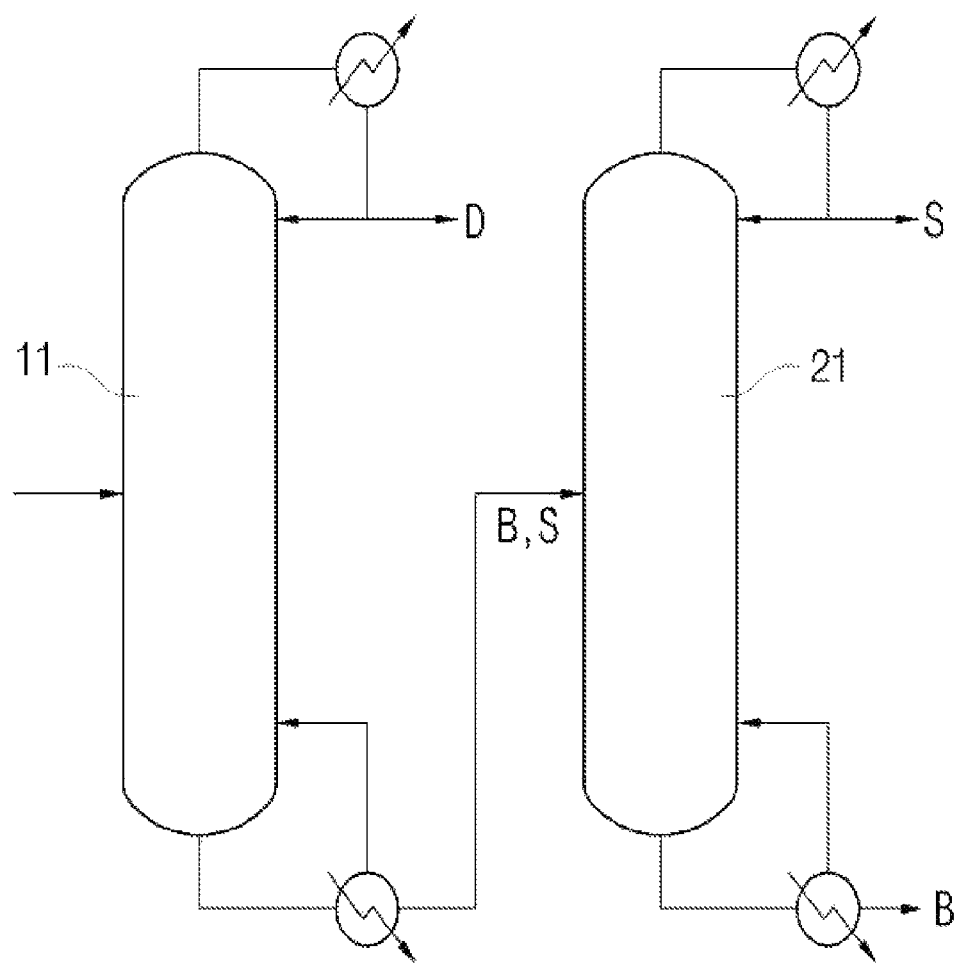
FIG. 1 is a schematic view of a conventional distillation process of separating a three-component mixture.
Figure 2:
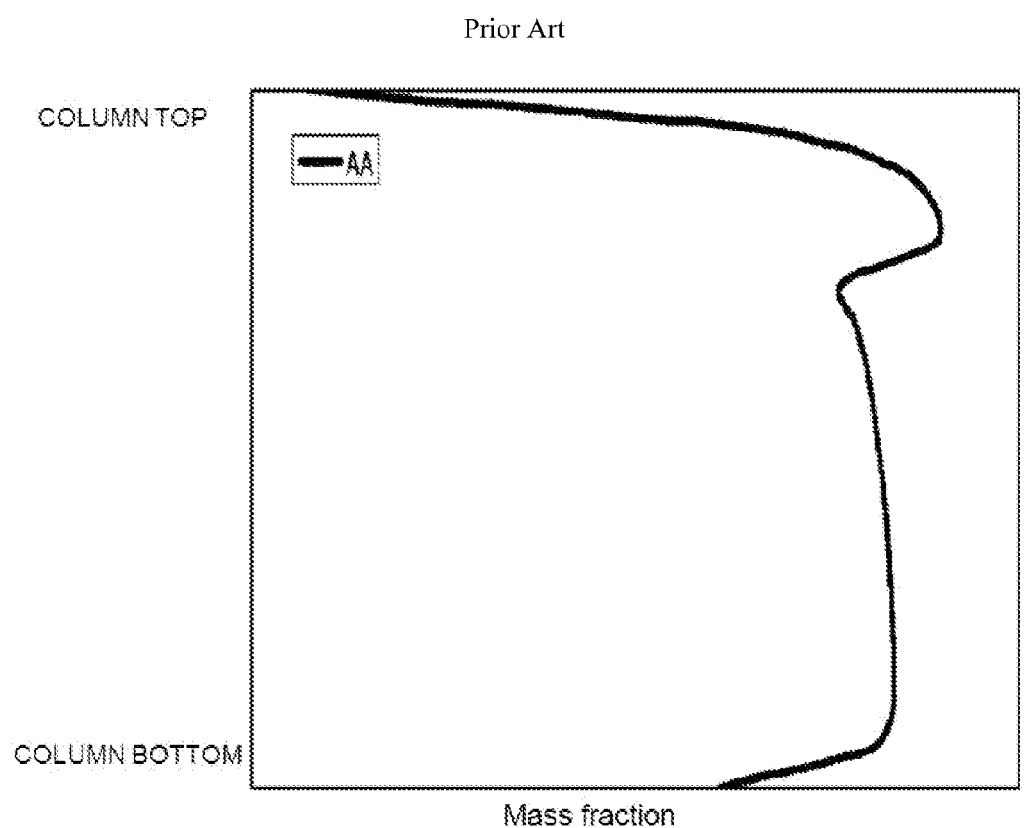
FIG. 2 shows a compositional profile of a middle boiling point component (acrylic acid) in a first column in a conventional distillation process.
Figure 3:
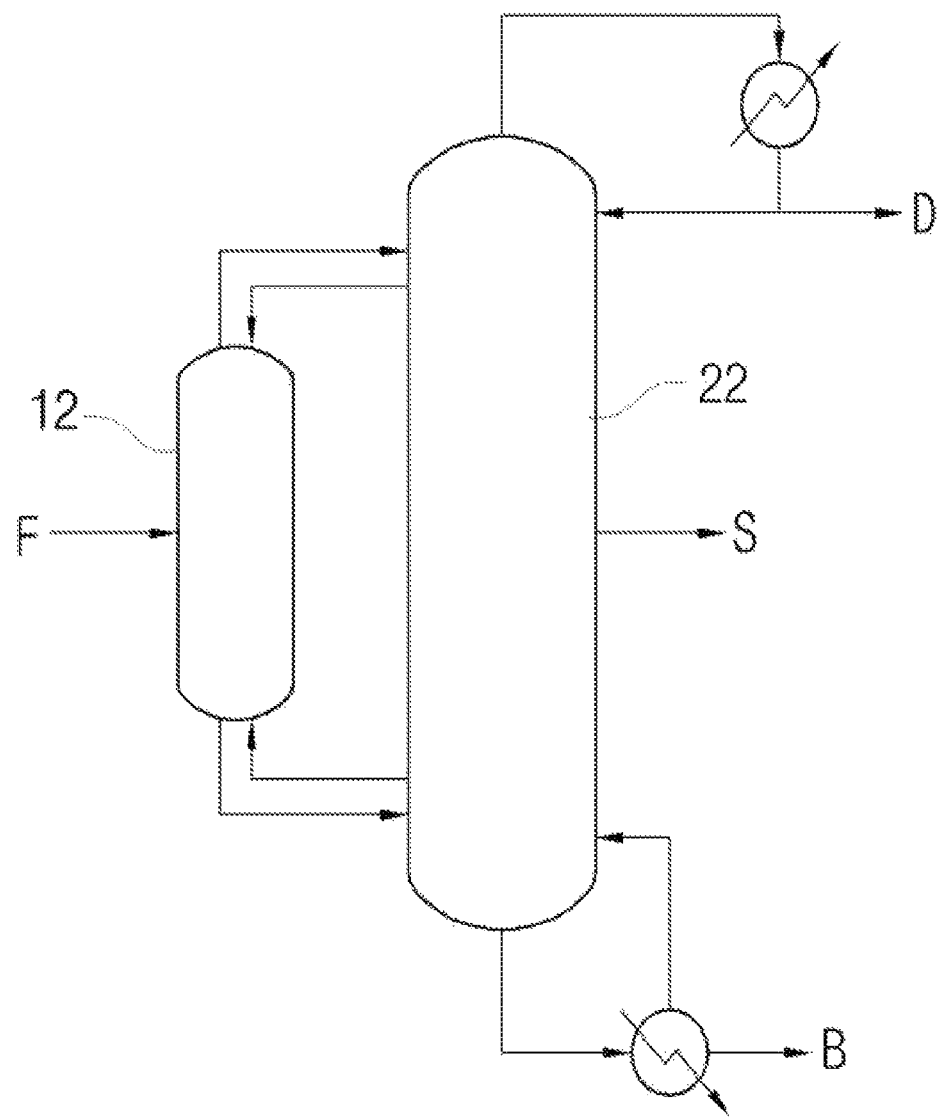
FIG. 3 is a schematic view showing a structure of a Petlyuk distillation column
Figure 4:
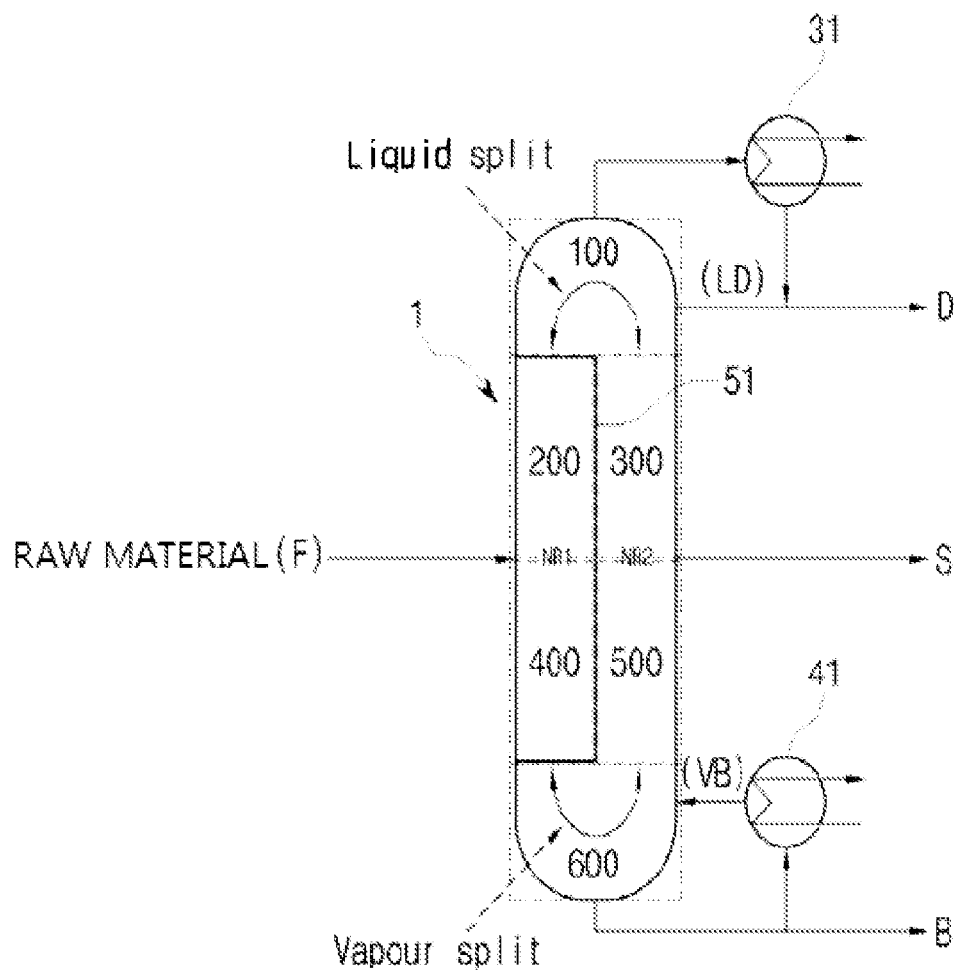
FIG. 4 is a schematic view showing a structure of a dividing wall distillation column according to the present invention.

A structure of the dividing wall distillation column according to the present invention is shown in FIG. 4.

The distillation column of the present invention includes a condenser 31 and a reboiler 41.

The condenser serves to condense a mixture in a gas state by depriving the mixture of evaporation heat. Here, a condenser used in a conventional chemical engineering system may be used without limitation.

The reboiler serves to vaporize a mixture in a liquid state by providing evaporation heat to the mixture. Here, a reboiler used in a conventional chemical engineering system may be used without limitation.

The main column 1 may be mainly divided into 6 sections.

The column-top zone 100 refers to an upper section of the main column that does not have a dividing wall installed therein.

The upper feed zone 200 is one of sections divided by the dividing wall, and is a sub-section arranged above a stream of an inflow material (raw material).

The upper outflow zone 300 is one of sections divided by the dividing wall, and is a sub-section arranged above a stream of an outflow material.

The lower feed zone 400 is the other one of the sections divided by the dividing wall, and is a sub-section arranged under a stream of the inflow material.

The lower outflow zone 500 is the other one of the sections divided by the dividing wall, and is a sub-section arranged under a stream of the outflow material.

The column-bottom zone 600 refers to a lower section of the main column which does not have a dividing wall installed therein.

The main column has at least one inflow point and at least three outflow points.

A raw material (F) such as crude acrylic acid flows in a middle inflow plate NR1 in which the upper feed zone and the lower feed zone come in contact with each other, a low boiling point component (D) flows out from the column-top zone, a high boiling point component (B) flows out from the column-bottom zone, and a middle boiling point component (S) flows out through a middle outflow plate NR2 in which the upper outflow zone and the lower outflow zone come in contact with each other. In this case, the middle boiling point component (S) is acrylic acid.

Here, the term "crude acrylic acid raw material" refers to a target material (material to be distilled) used in the distillation process known in the art, which is a mixture including acrylic acid as a main component, and the term "main component" refers to one component which is included in the largest amount among the respective components of the mixture. In order to obtain high-purity acrylic acid, the crude acrylic acid raw material preferably has a higher acrylic acid content, and in order to obtain at least 99% by weight of the high-purity acrylic acid, the crude acrylic acid raw material preferably has an acrylic acid content of at least 90% by weight.

According to the present invention, the expression "a middle boiling point component (S) is acrylic acid," means that acrylic acid is not 100% present but substantially present in the crude acrylic acid raw material. The expression "acrylic acid is substantially present in the crude acrylic acid raw material," means that a mixture itself is substantially considered acrylic acid, particularly that the mixture includes acrylic acid as a main component and has a higher acrylic acid content than a fed raw material.

This dividing wall distillation process has lower energy consumption than a conventional distillation process using two continuous distillation columns, which may be derived from a structural difference. In the dividing wall distillation column, since spaces divided by the dividing wall serve as a preliminary separator, a composition of a liquid substantially corresponds to an equilibrium distillation curve due to separation of the high boiling point component and the low boiling point component, and a thermodynamic efficiency for separation is good due to suppression of a remixing effect.

The upper feed zone and the lower feed zone play a similar role as the preliminary separator which is operated in a conventional process (i.e., the upper feed zone and the lower feed zone may be generally referred to as a preliminary divisional section). A three-component mixture flowing in the preliminary divisional section is separated into a low boiling point component and a high boiling point component. Some of the low boiling point component and the high boiling point component separated in the preliminary divisional section flows in the column-top zone and the column-bottom zone, and some flows back in the upper outflow zone and the lower outflow zone and is re-distilled.

The upper outflow zone and the lower outflow zone serve as a main separator which is operated in a conventional process (i.e., the upper outflow zone and the lower outflow zone may be generally referred to as a main divisional section). Mainly, the low boiling point component and the middle boiling point component are separated in an upper portion of the dividing wall of the main divisional section, and the middle boiling point component and the high boiling point component are separated in a lower portion of the dividing wall.

The low boiling point component is passed through the column-top zone of the main column and the condenser, and some of the low boiling point component is then produced into a low boiling point product (D), and the rest flows back to the column-top zone of the main column at a liquid flux (LD). The high boiling point component is passed through the column-bottom zone of the main column and the reboiler, and some of the high boiling point component is then produced into a high boiling point product (B), and the rest flows back to the column-bottom zone of the main column at a vapor flux (VB).

The design of a thermally coupled distillation column system having a dividing wall is based on the design of a conventional thermally coupled distillation column, and the design of a distillation column having a minimum number of plates. The efficiency of the distillation column is maximal when a liquid compositional distribution of distillation plates in the distillation column is similar to an equilibrium distillation curve. Therefore, a minimum-plate distillation system is first designed on the assumption that a distillation column is operated under a pre-reflux handling. That is to say, the upper feed zone and the lower feed zone are designed on the assumption that a composition of a liquid is identical to that of a raw material in a raw material feed plate. Also, in the upper outflow zone and the lower outflow zone, a liquid composition is calculated from the middle to the column top of the distillation column using a cascade method for designing an equilibrium composition, starting from a concentration of the middle boiling point product. In the lower outflow zone serving as the main separator, a liquid composition is calculated from the middle to the column bottom of the distillation column using a cascade method of calculating an equilibrium composition, starting from a concentration of the middle boiling point product. Then, the plate number of the upper feed zone and the lower feed zone, which serve as the preliminary separator, and the plate number of the upper outflow zone and lower outflow zone, which serve as the main separator, may be determined from the distribution of the obtained liquid composition, respectively, by counting the number of raw material feed plates and the number of plates having a composition of a product. Here, since the obtained number of the plates in the distillation column is an ideal theoretical plate number, the plate number in the distillation column is preferably in a range of 80 to 150% of the theoretical plate number, depending on the conventional design standard. When the plate number is less than 80% of the calculated theoretical plate number, the low boiling point and high boiling point components are not easily separated in the preliminary divisional section, whereas when the plate number exceeds 150%, an energy-reducing effect is not increased as a section having a minimum reflux ratio, resulting in an increase in investment costs.

Also, a length of the dividing wall installed in the main column does not have a fixed value, and may be freely varied according to the kinds and components of a raw material t be processed. The length of the dividing wall is preferably determined according to the total theoretical plate number calculated based on the distillation curves of the upper feed zone and the lower feed zone.

In such a dividing wall distillation column, there are various methods of calculating the theoretical plate number and amount of reflux by determining a spacing of the dividing wall using an equilibrium distillation curve method on a liquid composition with the preliminary divisional section and the main divisional section so as to design an optimal spacing of the dividing wall. However, the Fenske-Underwood equation is used to calculate the theoretical plate number according to the present invention (the Fenske-Underwood equation is widely known to those skilled in the art).

The length of the dividing wall is preferably in a range of 30 to 85% of the total theoretical plate number of the column-top zone, the upper feed zone, the lower outflow zone and the column-bottom zone, which are calculated based on the distillation curve. When the length of the dividing wall is less than 30%, some of the low boiling point component flows down from the preliminary divisional section, and may be introduced into a product in the main separator. On the other hand, when the length of the dividing wall exceeds 85%, it is difficult to maintain smooth equilibrium flow of liquid/vapor states of the low boiling point/middle boiling point components and liquid/vapor states of the middle boiling point/high boiling point components in the distillation column, which makes it difficult to manufacture a distillation column.

In the main column, a temperature of the column-top zone is preferably in a range of 55 to 65° C. at a pressure of 4.666 kPa. When the temperature of the column-top zone is less than 55° C., the low boiling point component (Light) may flow down from the preliminary divisional section, which affects the purity degree of a product. When the temperature of the column-top zone exceeds 65° C., the high boiling point component (Heavies) may flow up from the preliminary divisional section, which affects the purity degree of a product.

In the main column, a temperature of the column-bottom zone is preferably in a range of 90 to 100° C. at a pressure of 4.666 kPa. When the temperature of the column-bottom zone is less than 90° C., a middle boiling point component (acrylic acid) flows downwards as a product, which results in a decrease in production of the product. When the temperature of the column-bottom zone exceeds 100° C., a high boiling point component may laterally flow with the middle boiling point component (acrylic acid).

A temperature of the middle outflow plate NR2, which is provided in a position where the upper outflow zone and the lower outflow zone come in contact with each other, and from which the middle boiling point component (S) flows out, is preferably in a range of 73 to 83° C. at a pressure of 4.666 kPa. When the temperature of the middle outflow plate NR2 is less than 73° C., it is difficult to remove a low boiling point component, whereas, when the temperature of the middle outflow plate NR2 exceeds 83° C., it is difficult to remove a high boiling point component, which affects the purity degree of a product.

In the main column, the temperature ranges of the column-top zone, the column-bottom zone and the middle outflow plate NR2 are based on a pressure of 4.666 kPa (i.e., a pressure somewhat reduced from a normal pressure). When the distillation column is operated at a more reduced or compressed pressure than the pressure of 4.666 kPa, the temperature range may be varied. In general, the higher a pressure is, the higher an upper temperature limit and a lower temperature limit are.

In particular, when the column-top zone is out of a pressure of this pressure range, the temperature of the column-top zone may be in a range of an upper temperature limit ($T_{1\alpha}$) and a lower temperature limit ($T_{2\alpha}$), as calculated according to the following Equation 1:

$$\text{Lower limit: } T_{1\alpha}=21.5052*P^{0.2628}$$

$$\text{Upper limit: } T_{2\alpha}=29.3928*P^{0.2222} \qquad \text{Equation 1}$$

(wherein $T_{1\alpha}$ and $T_{2\alpha}$ represent temperatures (° C.); P represents a pressure (kPa), provided that $1.333 \leq P \leq 13.332$ and $P \neq 4.666$).

Also, when the column-bottom zone is out of a pressure of this pressure range, the temperature of the column-bottom zone may be in a range of a lower temperature limit ($T_{1\beta}$) to an upper temperature limit ($T_{2\beta}$), as calculated according to the following Equation 2:

$$\text{Lower limit: } T_{1\beta}=56.3053*P^{0.1293}$$

$$\text{Upper limit: } T_{2\beta}=65.6035*P^{0.1163} \qquad \text{Equation 2}$$

(wherein $T_{1\beta}$ and $T_{2\beta}$ represent temperatures (° C.); P represents a pressure (kPa), provided that $1.333 \leq P \leq 13.332$ and $P \neq 4.666$).

Additionally, when the middle outflow plate NR2 is out of a pressure of this pressure range, the temperature of the middle outflow plate NR2 may be in a range of an upper temperature limit ($T_{1\chi}$) and a lower temperature limit ($T_{2\chi}$), as calculated according to the following Equation 3:

Lower limit: $T_{1\chi}=44.8814*P^{0.1376}$

Upper limit: $T_{2\chi}=55.0983*P^{0.1211}$  Equation 3

(wherein $T_{1\chi}$ and $T_{2\chi}$ represent temperatures (° C.); P represents a pressure (kPa), provided that $1.333 \le P \le 13.332$ and $P \ne 4.666$).

As described above, the operation conditions of the dividing wall distillation column according to the present invention, which reflect the temperatures of the column-top zone, the column-bottom zone and the middle outflow plate according to a variation in pressure, are listed as follows.

| Pressure = 4.666 kPa | Lower limit | Upper limit |
|---|---|---|
| Temperature (° C.) of column-top zone | 55 | 65 |
| Temperature (° C.) of column-bottom zone | 90 | 100 |
| Temperature (° C.) of middle outflow plates | 73 | 83 |

| Pressure = 3.333 kPa | Lower limit | Upper limit |
|---|---|---|
| Temperature (° C.) of column-top zone | 50 | 60 |
| Temperature (° C.) of column-bottom zone | 85 | 95 |
| Temperature (° C.) of middle outflow plate | 70 | 80 |

| Pressure = 6.666 kPa | Lower limit | Upper limit |
|---|---|---|
| Temperature (° C.) of column-top zone | 60 | 70 |
| Temperature (° C.) of column-bottom zone | 93 | 103 |
| Temperature (° C.) of middle outflow plate | 77 | 87 |

As described above, the thermally coupled distillation column having a dividing wall according to the present invention is designed to improve the efficiency of the distillation column in a distillation system for distilling a mixture of three or more components. Therefore, the distillation column has the same effect as that obtained from the use of two distillation columns since a dividing wall is installed in the main column to form spaces having a liquid compositional distribution similar to the high-efficiency equilibrium distillation system and serving as the preliminary separator and the main separator.

Meanwhile, the present invention is directed to a method of fractionally distilling 2-ethyl hexanol. Here, the method includes producing acrylic acid using the above-described dividing wall distillation column.

MODE FOR INVENTION

Hereinafter, the present invention will be described in further detail with reference to the following Examples. It should be understood that the descriptions proposed herein are merely preferable examples for the purpose of illustration only, and not intended to limit the scope of the invention.

Example 1

In order to verify the performances of the distillation systems proposed in the present invention, a dividing-wall distillation column (DWC) was designed and operated. It was confirmed that it is possible to obtain a composition of a product required through an actual operation of the system. Two conventional distillation columns having no dividing wall were used in Comparative Example 1, and one distillation column provided with a dividing wall was used in Example 1. A content of acrylic acid in the raw material was set to 92.7% by weight in both of Comparative Example 1 and Example 1.

Figure 5:
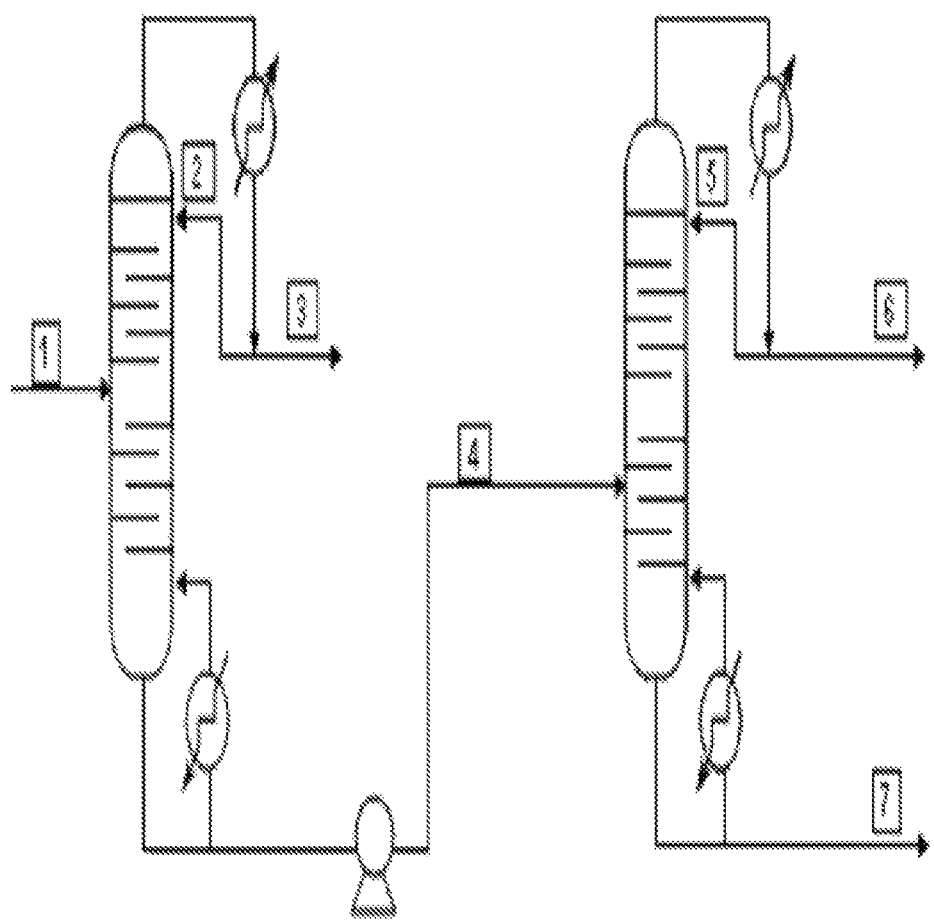
FIG. 5 is a schematic view showing a dividing wall distillation column described in Comparative Example 1.
Figure 6:
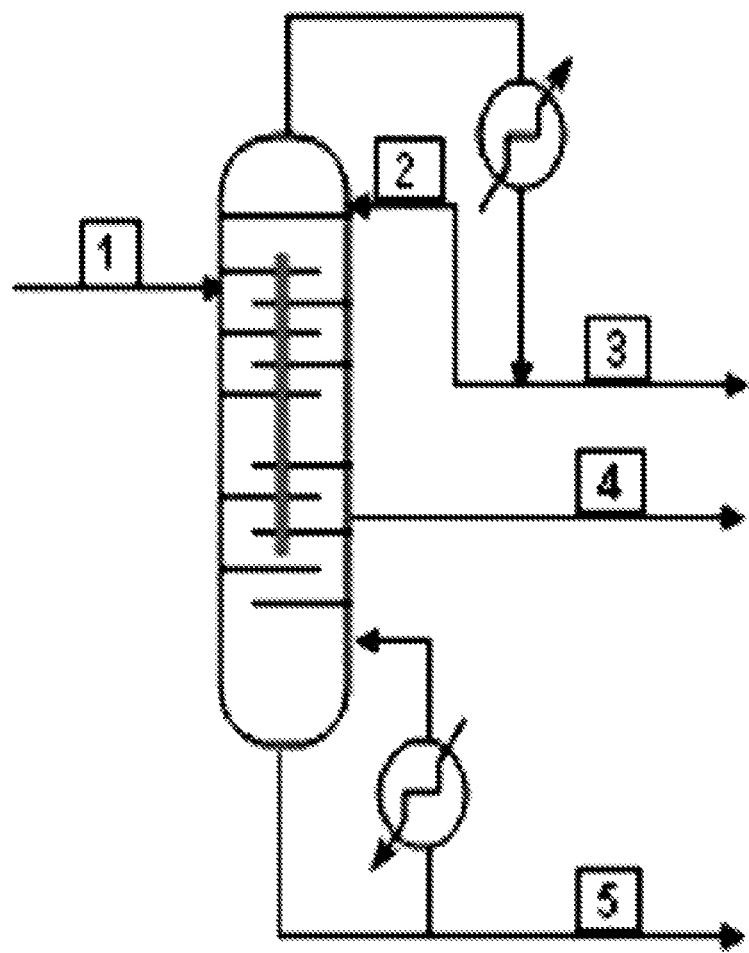
FIG. 6 is a schematic view showing a dividing wall distillation column described in Example 1.

The distillation columns described in Comparative Example 1 and Example 1 are shown in FIGS. 5 and 6, respectively. Reference numerals 1 to 7 in FIGS. 5 and 6 represent respective streams as described in Example 1 and Comparative Example 1.

Figure 7:
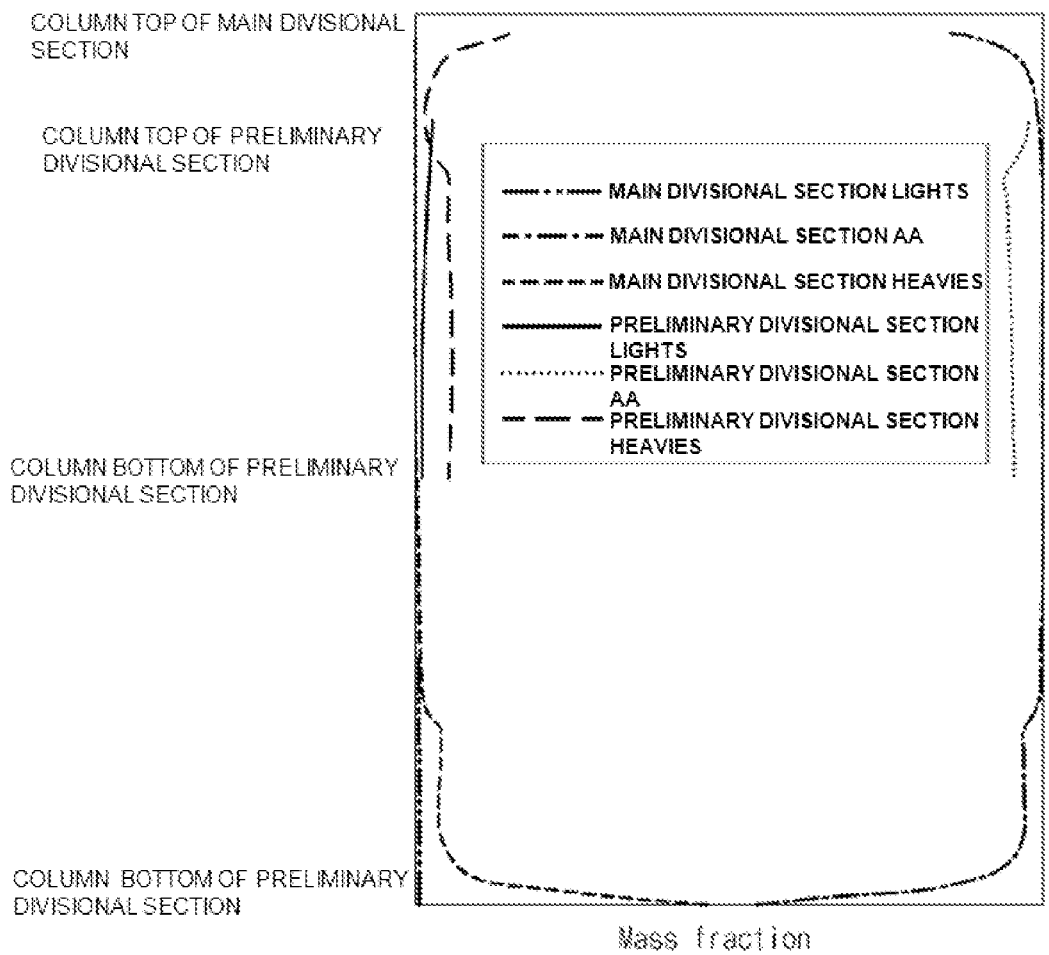
FIG. 7 is a compositional profile in a main column of the dividing wall distillation column according to the present invention.

FIG. 7 shows a compositional profile in the DWC according to the present invention.

The distillation columns of Example 1 and Comparative Example 1 had theoretical plate numbers as listed in Table 1. In the distillation column of Example 1, a length of the dividing wall was set to the theoretical plate number of 21, which corresponded to 84% of the total theoretical plate number in the column-top zone, the upper feed zone, the lower outflow zone and the column-bottom zone.

The experimental results are listed in the following Tables 2 and 3.

TABLE 1

|  |  | Theoretical plate number |
|---|---|---|
| Example | Column-top zone 100 | 5 |
|  | Upper feed zone 200 | 4 |
|  | Upper outflow zone 300 | 27 |
|  | Lower feed zone 400 | 17 |
|  | Lower outflow zone 500 | 9 |
|  | Column-bottom zone 600 | 7 |
| Comparative Example | First column | 20 |
|  | Second column | 25 |

TABLE 2

|  |  |  | Units | 1 | 2 | 3 | 4 | 5 | 6 | 7 |
|---|---|---|---|---|---|---|---|---|---|---|
| Comparative Example | Condition | Temperature | ° C. | 50.0 | 55.2 | 55.2 | 84.7 | 62.5 | 62.5 | 96.5 |
|  |  | Pressure | kPa | 196.131 | 4.666 | 4.666 | 395.527 | 4.666 | 4.666 | 13.332 |
|  |  | Flow rate | kg/hr | 5129.6 | 6464.94 | 610.0 | 4519.6 | 3959.2 | 3920 | 599.6 |
|  | Composition | Light | wt % | 1.80 | 14.80 | 14.80 | 0.00 | 0.00 | 0.00 | 0.00 |
|  |  | AA |  | 92.70 | 85.20 | 85.20 | 93.80 | 99.90 | 99.90 | 53.60 |
|  |  | Heavies |  | 5.40 | 0.00 | 0.00 | 6.20 | 0.00 | 0.00 | 46.40 |
| Example | Condition | Temperature | ° C. | 50.0 | 55.2 | 55.2 | 77.2 | 93.9 | — | — |
|  |  | Pressure | kPa | 196.131 | 4.666 | 4.666 | 9.306 | 11.999 | — | — |
|  |  | Flow rate | kg/hr | 5129.6 | 8063.5 | 610.0 | 3920.0 | 599.6 | — | — |

TABLE 2-continued

| | | Units | 1 | 2 | 3 | 4 | 5 | 6 | 7 |
|---|---|---|---|---|---|---|---|---|---|
| Composition | Light AA | wt % | 1.80 | 14.90 | 14.90 | 0.00 | 0.00 | — | — |
| | AA | | 92.70 | 85.10 | 85.10 | 99.90 | 53.70 | — | — |
| | Heavies | | 5.40 | 0.00 | 0.00 | 0.10 | 46.40 | — | — |

*AA: acrylic acid (Acrylic Acid)

TABLE 3

| | Comparative Example | | | | Reduction | Reduction |
|---|---|---|---|---|---|---|
| | Total | First column | Second Column | Example | (MMKcal/hr) | rate (%) |
| Energy consumption (MMK cal/hr) | 1.48 | 0.78 | 0.70 | 0.93 | 0.55 | 37.2 |

As described in Example 1, it was revealed that the high-purity acrylic acid was effectively recovered due to suppression of the remixing effect and an increase in separation efficiency. An additional recycling process of refining 2-ethyl hexanol is not required due to an increase in purity degree of the product, thereby improving the productivity. The inventive DWC (one column and two heat exchangers) was much less expensive than the conventional distillation columns (two columns and four heat exchangers) in an aspect of the investment costs.

A reduction rate of energy was highly decreased by approximately 37.2%, compared to the conventional distillation columns.

The present invention has been described in detail. However, it should be understood that the detailed description and specific examples, while indicating preferred embodiments of the invention, are given by way of illustration only, since various changes and modifications within the scope of the invention will become apparent to those skilled in the art from this detailed description.

The invention claimed is:

1. A dividing wall distillation column comprising a condenser, a reboiler and a main column having a dividing wall,
    wherein the main column is divided into a column-top zone, an upper feed zone, an upper outflow zone, a lower feed zone, a lower outflow zone and a column-bottom zone,
    a raw material having an acrylic acid content of 90% by weight or more flows in a middle inflow plate in which the upper feed zone and the lower feed zone come in contact with each other, a low boiling point component flows out from the column-top zone, a high boiling point component flows out from the column-bottom zone, and a middle boiling point component flows out through a middle outflow plate in which the upper outflow zone and the lower outflow zone come in contact with each other,
    wherein the middle boiling point component is acrylic acid,
    wherein the number of plates provided respectively in the column-top zone, the upper feed zone, the upper outflow zone, the lower feed zone, the lower outflow zone and the column-bottom zone is in a range of 80 to 150% of a theoretical plate number, as calculated from a distillation curve,
    wherein a length of the dividing wall is in a range of 30 to 85% of the total theoretical plate number in the column-top zone, the upper feed zone, the lower outflow zone and the column-bottom zone, as calculated from the distillation curve,
    wherein a temperature of the column-top zone is in a range of 55 to 65° C. at a pressure of 4.666 kPa, in a range of 50 to 60° C. at a pressure of 3.333 kPa, and in a range of 60 to 70° C. at a pressure of 6.666 kPa,
    wherein a temperature of the column-bottom zone is in a range of 90 to 100° C. at a pressure of 4.666 kPa, in a range of 85 to 95° C. at a pressure of 3.333 kPa, and in a range of 93 to 103° C. at a pressure of 6.666 kPa, and
    wherein a temperature of the middle outflow plate is in a range of 73 to 83° C. at a pressure of 4.666 kPa, in a range of 70 to 80° C. at a pressure of 3.333 kPa, and in a range of 77 to 87° C. at a pressure of 6.666 kPa.

2. A method of fractionally distilling acrylic acid comprising:
    producing acrylic acid using the dividing wall distillation column defined of claim 1.

* * * * *